(12) United States Patent
Fischer

(10) Patent No.: US 8,841,445 B2
(45) Date of Patent: Sep. 23, 2014

(54) PROCESS FOR PREPARING PURIFIED CAPROLACTAM FROM THE BECKMANN REARRANGEMENT OF CYCLOHEXANE OXIME

(71) Applicant: BASF SE, Ludwigshafen (DE)

(72) Inventor: Rolf-Hartmuth Fischer, Heidelberg (DE)

(73) Assignee: BASF SE (DE)

( * ) Notice: Subject to any disclaimer, the term of this patent is extended or adjusted under 35 U.S.C. 154(b) by 0 days.

(21) Appl. No.: 14/132,082

(22) Filed: Dec. 18, 2013

(65) Prior Publication Data

US 2014/0171638 A1    Jun. 19, 2014

Related U.S. Application Data

(60) Provisional application No. 61/739,027, filed on Dec. 19, 2012.

(51) Int. Cl.
*C07D 201/16* (2006.01)

(52) U.S. Cl.
CPC .................................. *C07D 201/16* (2013.01)
USPC .......................................................... 540/540

(58) Field of Classification Search
USPC .......................................................... 540/540
See application file for complete search history.

(56) References Cited

U.S. PATENT DOCUMENTS

| | | | |
|---|---|---|---|
| 4,301,073 A | 11/1981 | Fuchs et al. | |
| 6,849,731 B2 * | 2/2005 | Dsinter-De Hondt et al. | 540/540 |
| 2005/0011744 A1 | 1/2005 | Jetten et al. | |

FOREIGN PATENT DOCUMENTS

| | | |
|---|---|---|
| DE | 202870 A1 | 10/1983 |
| EP | 0 022 161 A1 | 1/1981 |
| WO | WO-03/018550 A1 | 3/2003 |
| WO | WO-03/045911 A1 | 6/2003 |

OTHER PUBLICATIONS

International Search Report for PCT/EP2013/076829 dated Mar. 5, 2014.

* cited by examiner

*Primary Examiner* — Bruck Kifle
(74) *Attorney, Agent, or Firm* — Drinker Biddle & Reath LLP

(57) ABSTRACT

A process is described for preparing purified caprolactam, comprising the steps
  a) extraction of crude caprolactam, obtained from the Beckmann rearrangement of cyclohexanone oxime, with an organic extractant,
  b) removal of the organic phase from step a),
  c) distillative separation of the organic extractant from the organic phase from step b) giving rise to water-containing lactam extract, being preceded by addition of the distillative separation, aqueous alkali metal hydroxide solution in an amount of from 0 to 10 mmol/kg of caprolactam,
  d) addition of 0 to 30 mmol of alkali metal hydroxide/kg of caprolactam to the water-containing lactam extract from step c),
  e) distillative removal of water from the water-containing lactam extract treated with alkali metal hydroxide from step d),
  f) freeing the caprolactam from step e) from by-products lower- and higher-boiling than caprolactam by distillation,
with addition in steps c) and d) together of at least 1.5 mmol of alkali metal hydroxide/kg of caprolactam.

8 Claims, No Drawings

PROCESS FOR PREPARING PURIFIED CAPROLACTAM FROM THE BECKMANN REARRANGEMENT OF CYCLOHEXANE OXIME

CROSS-REFERENCE TO RELATED APPLICATIONS

This application claims the benefit of U.S. Provisional Application 61/739,027, filed Dec. 19, 2012, which is incorporated herein by reference.

The present application relates to a process for purifying caprolactam or preparing purified caprolactam, which is obtained by Beckmann rearrangement of cyclohexanone oxime with concentrated sulfuric acid or oleum. The hydroxylammonium sulfate required for the oximation of cyclohexanone is preferably prepared by hydrogenation of nitrogen monoxide with hydrogen in dilute sulfuric acid over catalysts comprising palladium or platinum. The oximation of cyclohexanone is effected with hydroxylammonium sulfate with continuous addition of ammonia.

Two processes are carried out industrially for preparing caprolactam by rearrangement of cyclohexanone oxime with sulfuric acid or oleum in the liquid phase to give caprolactam sulfate. They differ principally in the preparation of the hydroxylammonium salt and of the cyclohexanone oxime, by the conditions in the oximation and accordingly also in the purification of the caprolactam sulfate, obtained from the Beckmann rearrangement, to give pure caprolactam (J. Ritz et al., Ullmann's Encyclopedia of Industrial Chemistry, 6th Ed., Vol. 6, pp. 185 to 205).

It is known that nitrate ions can be hydrogenated with hydrogen the so-called HPO process, in the presence of a palladium catalyst and a phosphate buffer solution, to give a hydroxylammonium salt, which is then reacted with cyclohexanone to give cyclohexanone oxime. The phosphate buffer solution released is mixed again with nitric acid and fed back into the hydrogenation (Hans-Jürgen Arpe, Industrielle Organische Chemie (Industrial Organic Chemistry), Wiley-VCH-Verlag (Publisher), 6th Ed., pp. 280 to 283).

The Beckmann rearrangement of the cyclohexanone oxime is carried out with sulfuric acid or oleum. The caprolactam sulfate prepared in this case and excess sulfuric acid are reacted with ammonia to give caprolactam and ammonium sulfate.

EP 1 423 361 B1 (DSM), page 5, [0031] teaches that, after oximation and Beckmann rearrangement, the caprolactam obtained from the reaction of the caprolactam sulfate with ammonia is removed by extractions. The extract stream is purified in a series of process steps. These steps include purification by ion exchange and by catalytic hydrogenation. A hydrogenation is conducted to convert unsaturated 7-membered ring lactams to caprolactam and thus to improve the caprolactam quality, as described, for example, in WO 03/045911.

Water is removed from the product stream comprising about 85% by weight of caprolactam, about 15% by weight of water and small amounts of impurities, in a series of evaporators, where the temperatures in the evaporators are between 80 and 125° C. The total residence time in the evaporators is 3 hours.

The removal of water takes place in the presence of a total of less than 20 mmol of sodium hydroxide, in aqueous solution, per kg of caprolactam. The aqueous sodium hydroxide solution for this is added to the caprolactam prior to the evaporators. The aqueous sodium hydroxide solution is to react with caprolactam to give the Na-salt of 6-aminocaproic acid. This salt, according to DD-A-202870, has the same purification effect as sodium hydroxide, but, in contrast to sodium hydroxide, does not cause any caprolactam oligomerization.

The caprolactam stream now comprising only 0.5% by weight of water is distilled in two stages under reduced pressure. In the first stage, low-boiling impurities and water are removed in a first distillation column at a bottom temperature of 175° C., a pressure of 5.2 kPa and a residence time of several minutes. In a second distillation column, high-boiling impurities are removed in a column at a bottom temperature of 133° C., a pressure of 1.2 kPa and a residence time of one hour.

A disadvantage of the workup of the reaction output of the Beckmann rearrangement according to EP 1 423 361 B1 is the large number of purification steps: caprolactam extraction, caprolactam re-extraction, ion exchange, catalytic hydrogenation, removal of water, distillative caprolactam purification. These give rise to high capital, operating and maintenance costs. To be particularly emphasised here are the hydrogenation, for which the catalyst must have a high on-stream time, and the ion exchanger, which must be regularly regenerated. Moreover, no caprolactam is obtained corresponding to the standard specification, since the $E_{290}$ value is above 0.05.

The object therefore was to provide a process for the workup and purification of caprolactam, prepared by Beckmann rearrangement of cyclohexanone oxime with sulfuric acid or oleum, requiring a lower number of purification steps, giving rise to lower operating costs and preferably providing higher-quality caprolactam corresponding to the standard specification.

The object according to the invention is achieved by a process for preparing purified caprolactam, comprising the steps a) extraction of crude caprolactam, obtained from the Beckmann rearrangement of cyclohexanone oxime, with an organic extractant, b) removal of the organic phase from step a), c) distillative separation of the organic extractant from the organic phase from step b) giving rise to water-containing lactam extract, being preceded by addition of the distillative separation aqueous alkali metal hydroxide solution in an amount of 0 to 10 mmol of alkali metal hydroxide/kg caprolactam, d) addition of 0 to 30 mmol of alkali metal hydroxide/kg caprolactam to the water-containing lactam extract from step c), e) distillative removal of water from the water-containing lactam extract treated with alkali metal hydroxide, preferably NaOH, from step d), f) freeing the caprolactam from step e) from by-products lower- and higher-boiling than caprolactam by distillation, with addition in steps c) and d) together of at least 1.5 mmol of alkali metal hydroxide/kg of caprolactam. The total amount of alkali metal hydroxide added in the process is accordingly at least 2 mmol/kg of caprolactam.

The minimum amount of alkali metal hydroxide in steps c) and d) together is preferably in the range of 1.5 to 15 mmol of alkali metal hydroxide/kg of caprolactam.

Preference is given to the use of NaOH or KOH, particularly NaOH, as alkali metal hydroxide.

In step d), preferably 1.5 to 30 mmol, more preferably 1.75 to 20 mmol, particularly preferably 1.75 to 14 mmol, especially 1.75 to 10 mmol of alkali metal hydroxide, preferably NaOH, per kg of caprolactam are added.

The residence time in step e) is preferably less than 30 minutes, particularly preferably less than 20 minutes.

The organic solvent in step a) is preferably toluene or benzene.

In step e) and/or f) the bottom temperature preferably does not exceed 160° C., particularly preferably 150° C.

The caprolactam after water removal at the end of step e) preferably comprises 0.15 to 0.25% by weight of water.

The pressure in step e) is preferably 20 to 100 mbar, particularly preferably 30 to 60 mbar (top pressure), in at least one distillation stage.

The pressure in step f) is preferably 2 to 20 mbar, particularly preferably 4 to 10 mbar, especially 5 to 8 mbar (top pressure).

In step c), preferably 0.5 to 6 mmol, more preferably 1 to 4 mmol, particularly preferably 2 to 3 mmol, especially preferably 2.5 mmol, of alkali metal hydroxide/kg caprolactam are added.

According to one embodiment of the invention the total amount of alkali hydroxide added in steps c) and d) is at most 14 mmol, preferably at most 12.5 mmol alkali hydroxide, preferably NaOH/kg caprolactam.

The cyclohexanone oxime used in the Beckmann rearrangement can be prepared by oximation of cyclohexanone with hydroxylammonium sulfate. The hydroxylammonium sulfate is preferably obtained by catalytic hydrogenation of nitrogen monoxide in the presence of sulfuric acid.

The individual steps for preparing caprolactam and for the purification are illustrated in detail in the following.

Beckmann Rearrangement of Cyclohexanone Oxime (a)

The cyclohexanone required for the preparation of cyclohexanone oxime can be obtained by cyclohexane oxidation with air to give a mixture of cyclohexanol and cyclohexanone ("anolone"), distillative separation of the anoione into cyclohexanol and cyclohexanone and dehydrogenation of the cyclohexanol to cyclohexanone.

It is further possible to hydrogenate phenol in one step to cyclohexanone.

Lastly, cyclohexanone can be prepared by hydration of cyclohexene to cyclohexanol and subsequent dehydrogenation of the cyclohexanol.

The hydroxylammonium sulfate used for the oximation of cyclohexanone is preferably obtained by hydrogenation of nitrogen monoxide with hydrogen, in the presence of (dilute) sulfuric acid, over catalysts comprising platinum or palladium.

The hydroxylammonium sulfate solution, preferably obtained by hydrogenation of nitrogen monoxide, is reacted with cyclohexanone and ammonia, i. e. under pH-controlled conditions, to give cyclohexanone oxime and ammonium sulfate.

For the Beckmann rearrangement of the cyclohexanone oxime, the latter is reacted continuously with concentrated (98%) sulfuric acid or oleum (sulfuric acid comprising excess sulfur trioxide).

The oxime melt and oleum are then introduced with cooling into product already rearranged. The caprolactam sulfate, formed by rapid reaction in the Beckmann rearrangement, and excess sulfuric acid are neutralized with aqueous ammonia. This forms a biphasic mixture comprising aqueous ammonium sulfate as the lower phase and 60 to 80% by weight of caprolactam and 20 to 40% by weight of water as the upper phase.

The two liquid phases are separated. The ammonium sulfate phase is dehydrated and crystallised.

Caprolactam Extraction and Extractant Recycling (a), (b), (c)

The aqueous crude caprolactam phase is extracted with an organic solvent, preferably toluene or benzene. This gives biphasic extracts. Solutions of caprolactam in toluene or benzene occur as the upper phase. Caprolactam-free water occurs as the lower phase, which may be used elsewhere in the process or is discarded.

Prior to the distillative separation of extractant and caprolactam, aqueous alkali metal hydroxide solution, which may be diluted, is preferably added to the extract. Preference is given to sodium hydroxide and potassium hydroxide, particularly sodium hydroxide, as alkali metal hydroxides. A sodium hydroxide solution is understood to be a 1 to 30% by weight, preferably 2 to 10% by weight, particularly 2.5 to 3% by weight aqueous solution. The alkali metal hydroxide is typically used in an amount of 0 to 10 mmol/kg of caprolactam, preferably 0.5 to 6 mmol/kg of caprolactam, preferably 1 to 4 mmol/kg of caprolactam.

The extractant is distilled off and fed back into the extraction step. The distillative removal of the extractant can be carried out in any suitable apparatus known to those skilled in the art. Suitable apparatuses for the distillation are as described, for example, in: Kirk-Othmer, Encyclopedia of Chemical Technology, 4th. Ed., Vol. 8, John Wiley & Sons, New York, 1996, pp. 334 to 348, such as sieve tray columns, bubble-cap tray columns, columns having structured packing or random packing, or single-stage evaporators, such as falling-film evaporators, thin-film evaporators, flash evaporators, multiphase helical tube evaporators, natural circulation evaporators or forced circulation flash evaporators. The distillation may be carried out in multiple, such as two or three, apparatuses, preferably in one apparatus.

For suitable conditions, reference may also be made to EP-B-1 423 361. A purification of the crude lactam or lactam extract or caprolactam by re-extraction and treatment with an ion exchanger and/or by hydrogenation is not performed according to the present invention.

Removal of Water from Caprolactam (d), (e)

The lactam extract obtained following distillative removal of the extractant comprises 70 to 99% by weight, preferably 85 to 99, particularly 90 to 98% by weight of caprolactam and 1 to 30% by weight, preferably 1 to 15% by weight, particularly 2 to 10% by weight of water.

To this water-containing lactam extract are added 0 to 30, preferably 1.5 to 30, more preferably 1.75 to 20, preferably 1.75 to 10, more preferably 1.75 to 7.5, particularly preferably 4 to 6 mmol of alkali metal hydroxide, preferably aqueous sodium hydroxide solution, per kilogram of caprolactam in the lactam extract, preferably in the form of 1 to 30% by weight, preferably 2 to 10% by weight, aqueous sodium hydroxide solution. Water is then removed by distillation from the caprolactam, where bottom temperatures of 160° C. are preferably not exceeded. In at least one distillation step, a pressure preferably in the range of 20 to 100 mbar is employed. The total residence time is preferably less than 30 minutes, particularly preferably than 20 minutes.

The largely water-free caprolactam still comprises preferably 0.15 to 0.25% by weight of water.

Caprolactam Distillation (f)

The largely dewatered caprolactam is subsequently distilled under reduced pressure such that the bottom temperature does not exceed 160° C. The pressure is preferably 2 to 20 mbar, particularly preferably 4 to 10 mbar, particularly 5 to 8 mbar. The caprolactam is freed from by-products lower- and higher-boiling than caprolactam during the distillation.

The caprolactam distillation can be carried out in any suitable apparatus known to those skilled in the art. Suitable apparatuses for the distillation are as described, for example, in: Kirk-Othmer, Encyclopedia of Chemical Technology, 4th. Ed., Vol. 8, John Wiley & Sons, New York, 1996, pp. 334 to 348, such as sieve tray columns, bubble-cap tray columns, columns having structured packing or random packing, or single-stage evaporators, such as falling-film evaporators, thin-film evaporators, flash evaporators, multiphase helical tube evaporators, natural circulation evaporators or forced circulation flash evaporators.

The invention is illustrated in detail by the following examples.

EXAMPLE 1

For the preparation of largely water-free caprolactam in a continuous process for preparing caprolactam by Beckmann rearrangement of cyclohexanone oxime, cyclohexanone was firstly reacted with hydroxylammonium sulfate solution, prepared by hydrogenation of nitrogen monoxide with hydrogen in the presence of dilute sulfuric acid and catalysts comprising palladium, to give cyclohexanone oxime. Excess sulfuric acid was neutralized with continuous addition of ammonia, and the ammonium sulfate formed was removed.

The cyclohexanone oxime thus obtained was rearranged with oleum to give caprolactam sulfate. Caprolactam sulfate and excess sulfuric acid were neutralized with ammonia.

The resulting biphasic mixture was separated, and an aqueous ammonium sulfate solution was removed and discharged.

The water-containing crude caprolactam phase was extracted with toluene as previously described. The biphasic extracts were separated from each other by phase separation. The aqueous phase was discarded. From the organic phase, which comprised the caprolactam, the toluene was removed by distillation following addition of 2.5 mmol of NaOH/kg of caprolactam and fed back into the extraction step. The lactam extract thus obtained comprised 4 to 10% by weight of water.

EXAMPLES 2A TO 2F

To the lactam extract obtained in example 1, having a water content of 4 to 10% by weight, was added a 2.5% by weight aqueous sodium hydroxide solution (1.25 to 10 mmol NaOH per kg of lactam extract) in the amounts given in Table 1. In two evaporators connected in series, water was removed from the lactam extract as described and purified by distillation in two columns under reduced pressure. In the first column, water and impurities lower-boiling than caprolactam were removed as top products.

The bottom product of the first column was further purified in a second distillation column. In this case the high-boiling impurities compared to caprolactam were drawn off from the bottom, and caprolactam meeting the specification was obtained.

TABLE 1

| Examples | mmol NaOH/ kg capro. | PAN | $E_{290}$ | VB meqOH⁻/kg | Alkalinity meqOH⁻/kg |
|---|---|---|---|---|---|
| 2a | 10 | 1.8 | 0.035 | 0.10 | 0.012 |
| 2b | 7.5 | 1.5 | 0.036 | 0.13 | 0.013 |
| 2c | 5.0 | 1.3 | 0.040 | 0.10 | 0.010 |
| 2d | 2.5 | 1.5 | 0.044 | 0.10 | 0.012 |
| 2e | 1.75 | 1.9 | 0.049 | 0.11 | 0.010 |
| V2f | 1.25 | 1.9 | 0.053 | 0.11 | 0.011 |

The determination of the values of PAN, $E_{290}$, VB (volatile bases) was conducted as described in EP-B-1 423 361 in Table 1, and that of the alkalinity by titration against a 0.01 molar aqueous HCl solution using Tashiro's indicator.

In Ullmann's Encyclopedia of Industrial Chemistry, $6^{th}$ ed., Vol. 6, p 200 the following values are given for the caprolactam standard specification:

Permanganate absorption number (PAN): max 5
Absorbance 290 nm ($E_{290}$): max 0.05
Volatile bases (VB): max 0.5 meq/kg The threshold values are met according to the inventive method.

Comparison between Table 1 in EP 1 423 361131 and Table 1 above Shows:

Despite the lower number of purification steps in the inventive process, the amounts of aqueous sodium hydroxide required to meet the caprolactam specification are only marginally higher than in EP 1 423 361 B1 (example 2e: 1.75 mmol NaOH/kg caprolactam compared to 0.3 mmol NaOH/kg caprolactam in EP 1 423 361 B1).

In addition, the process according to the invention affords better PAN and $E_{290}$ values than EP 1 423 361 B1.

Finally, the $E_{290}$ values in EP 1 423 361 B1, Examples II to IX,—in contrast to the present invention—do not meet the specification.

Although an improvement of the PAN and $E_{290}$ values with decreasing amounts of NaOH is observed in EP 1 423 361 B1, this is not the case according to the present invention. In example V2f with 1.25 mmol NaOH/kg of caprolactam, the $E_{290}$ specification is not met.

The invention claimed is:

1. A process for purifying caprolactam, comprising the steps
   a) extraction of crude caprolactam, obtained from the Beckmann rearrangement of cyclohexanone oxime, with an organic extractant,
   b) removal of the organic phase from step a),
   c) distillative separation of the organic extractant from the organic phase from step b) giving rise to water-containing lactam extract, the distillative separation being preceded by addition of aqueous alkali metal hydroxide solution in an amount of from 0.5 to 6 mmol/kg of caprolactam,
   d) addition of 0 to 30 mmol of alkali metal hydroxide/kg of caprolactam to the water-containing lactam extract from step c),
   e) distillative removal of water from the water-containing lactam extract treated with alkali metal hydroxide from step d),
   f) freeing the caprolactam from step e) from by-products lower- and higher-boiling than caprolactam by distillation,
   with addition in steps c) and d) together of at least 1.5 mmol of alkali metal hydroxide/kg of caprolactam.

2. The process according to claim 1, wherein 1.5 to 30 mmol of alkali metal hydroxide/kg of caprolactam are added in step d).

3. The process according to claim 1, wherein the residence time is less than 30 minutes in step e).

4. The process according to claim 1, wherein the organic solvent in step a) is toluene or benzene.

5. The process according to claim 1, wherein the bottom temperature in step e) and/or f) does not exceed 160° C.

6. The process according to claim 5, wherein the pressure in step e) is 20 to 100 mbar (top pressure) in at least one distillation stage.

7. The process according to claim 5, wherein the pressure in step f) is 2 to 20 mbar (top pressure).

8. The process according to claim 1, wherein the cyclohexanone oxime used in the Beckmann rearrangement is prepared by oximation of cyclohexanone with hydroxylammonium sulfate, obtained by catalytic hydrogenation of nitrogen monoxide in the presence of sulfuric acid.

* * * * *

UNITED STATES PATENT AND TRADEMARK OFFICE
CERTIFICATE OF CORRECTION

| | | |
|---|---|---|
| PATENT NO. | : 8,841,445 B2 | Page 1 of 1 |
| APPLICATION NO. | : 14/132082 | |
| DATED | : September 23, 2014 | |
| INVENTOR(S) | : Rolf-Hartmuth Fischer | |

It is certified that error appears in the above-identified patent and that said Letters Patent is hereby corrected as shown below:

On the Title Page:

Item 54, the Title should read --PROCESS FOR PREPARING PURIFIED CAPROLACTAM FROM THE BECKMANN REARRANGEMENT OF CYCLOHEXANONE OXIME--

Signed and Sealed this
Seventh Day of April, 2015

Michelle K. Lee
*Director of the United States Patent and Trademark Office*